US010617540B2

(12) United States Patent
Peterson et al.

(10) Patent No.: US 10,617,540 B2
(45) Date of Patent: Apr. 14, 2020

(54) STENTS FORMED FROM DISSIMILAR METALS FOR TISSUE GROWTH CONTROL

(71) Applicant: Medtronic Vascular, Inc., Santa Rosa, CA (US)

(72) Inventors: Justin Peterson, Santa Rosa, CA (US); Ryan Bienvenu, Santa Rosa, CA (US); Stefan Tunev, Santa Rosa, CA (US); Michael Harms, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 99 days.

(21) Appl. No.: 15/808,583

(22) Filed: Nov. 9, 2017

(65) Prior Publication Data
US 2018/0125631 A1 May 10, 2018

Related U.S. Application Data

(60) Provisional application No. 62/420,478, filed on Nov. 10, 2016.

(51) Int. Cl.
*A61F 2/88* (2006.01)
*A61F 2/90* (2013.01)
(Continued)

(52) U.S. Cl.
CPC .............. *A61F 2/88* (2013.01); *A61F 2/0077* (2013.01); *A61F 2/90* (2013.01); *A61F 2/915* (2013.01);
(Continued)

(58) Field of Classification Search
CPC .......... A61F 2/88–89; A61F 2250/0043–0045; A61F 2/915
See application file for complete search history.

(56) References Cited

U.S. PATENT DOCUMENTS

| 4,800,882 A | 1/1989 | Gianturco |
| 4,886,062 A | 12/1989 | Wiktor |

(Continued)

FOREIGN PATENT DOCUMENTS

| WO | 2008/063780 A2 | 5/2008 |
| WO | 2008/106223 A1 | 9/2008 |
| WO | 2014/162902 A1 | 10/2014 |

OTHER PUBLICATIONS

Cwikiel W et al, "Electrolytic Stents to Inhibit Tumor Growth. An experimental study in vitro and in rats," Acta Radiologica, Informa Healthcare, GB, vol. 34, No. 3, May 1, 1993 (May 1, 1993), pp. 258-262.

(Continued)

*Primary Examiner* — Rebecca S Preston
(74) *Attorney, Agent, or Firm* — Medler Ferro Woodhouse & Mills PLLC

(57) ABSTRACT

Stents formed from dissimilar materials configured to control tissue growth. A stent may be formed from a composite wire helically wound into a stent having a tubular configuration. The composite wire includes a first wire and a second wire coupled together, the first and second wires being formed from dissimilar metals such that a potential difference is formed when the dissimilar metals are exposed to bodily fluids. The potential difference is configured to inhibit cell proliferation and thereby control tissue growth around the stent after implantation. A stent may be formed from a hollow composite wire including an inner member that includes first and second longitudinal strips formed from dissimilar metals. A stent may be formed from a composite wire having a plurality of windows along a length of the composite wire. An insert formed from a dissimilar metal is disposed within each window of the plurality of windows.

20 Claims, 11 Drawing Sheets

(51) Int. Cl.
*A61F 2/915* (2013.01)
*A61F 2/00* (2006.01)
*A61L 31/02* (2006.01)
*A61L 31/16* (2006.01)

(52) U.S. Cl.
CPC ............ *A61L 31/022* (2013.01); *A61L 31/16* (2013.01); *A61F 2002/009* (2013.01); *A61F 2002/0086* (2013.01); *A61F 2002/0091* (2015.04); *A61F 2002/91575* (2013.01); *A61F 2210/0009* (2013.01); *A61F 2210/0076* (2013.01); *A61F 2230/0006* (2013.01); *A61F 2230/0019* (2013.01); *A61F 2250/003* (2013.01); *A61F 2250/0015* (2013.01); *A61F 2250/0032* (2013.01); *A61F 2250/0043* (2013.01); *A61F 2250/0051* (2013.01); *A61F 2250/0054* (2013.01); *A61F 2250/0059* (2013.01); *A61F 2250/0068* (2013.01); *A61F 2250/0071* (2013.01); *A61F 2250/0098* (2013.01); *A61L 2300/416* (2013.01)

(56) References Cited

U.S. PATENT DOCUMENTS

| | | |
|---|---|---|
| 5,019,090 A | 5/1991 | Pinchuk |
| 5,133,732 A | 7/1992 | Wiktor |
| 5,782,903 A | 7/1998 | Wiktor |
| 6,136,023 A | 10/2000 | Boyle |
| 7,167,746 B2 | 1/2007 | Pederson |
| 7,682,388 B2 | 3/2010 | Rea |
| 2007/0244536 A1 | 10/2007 | Pederson |
| 2007/0270942 A1 | 11/2007 | Thomas |
| 2009/0023004 A1 | 1/2009 | Pederson |
| 2009/0187254 A1 | 7/2009 | Deal et al. |
| 2010/0303882 A1 | 12/2010 | Cantrell et al. |
| 2011/0245904 A1 | 10/2011 | Pacetti et al. |
| 2011/0251668 A1* | 10/2011 | Thompson ............... A61F 2/90 623/1.15 |
| 2012/0067103 A1 | 3/2012 | Bienvenu et al. |
| 2013/0274864 A1 | 10/2013 | Bienvenu et al. |
| 2015/0297803 A1 | 10/2015 | Pulugurtha |

OTHER PUBLICATIONS

International Search Report and the Written Opinion of the International Searching Authority issued in PCT/US2017/060948, dated Feb. 12, 2018.

Lee, Jung-Jin et al., "Evaluation of Effect of Galvanic Corrosion Between Nickel-Chromium Metal and Titanium on Ion Release and Cell Toxicity" J Adv Prosthodont 2015;7:172-7, pp. 1-6.

Devine, D.M. et al., "Tissue Reaction to Implants of Different Metals: A Study Using Guide Wires in Cannulated Screws" www.ecmjournal.org, European Cells and Materials, vol. 18 2009 (pp. 40-48), pp. 40-48.

Sansone, Valerio et al., "The Effects on Bone Cells of Metal Ions Released From Orthopaedic Implants. A Review" Clinical Cases in Mineral and Bone Metabolism 2013; 10(1): 34-40.

Acevedo, Daniel, MD et al., "Mixing Implants of Differing Metallic Composition in the Treatment of Upper-Extremity Fractures" www.healio.com/orthopedics/journals/ortho, Orthopedics, Sep. 2013, vol. 36, Issue 9, e1175-e1179.

* cited by examiner

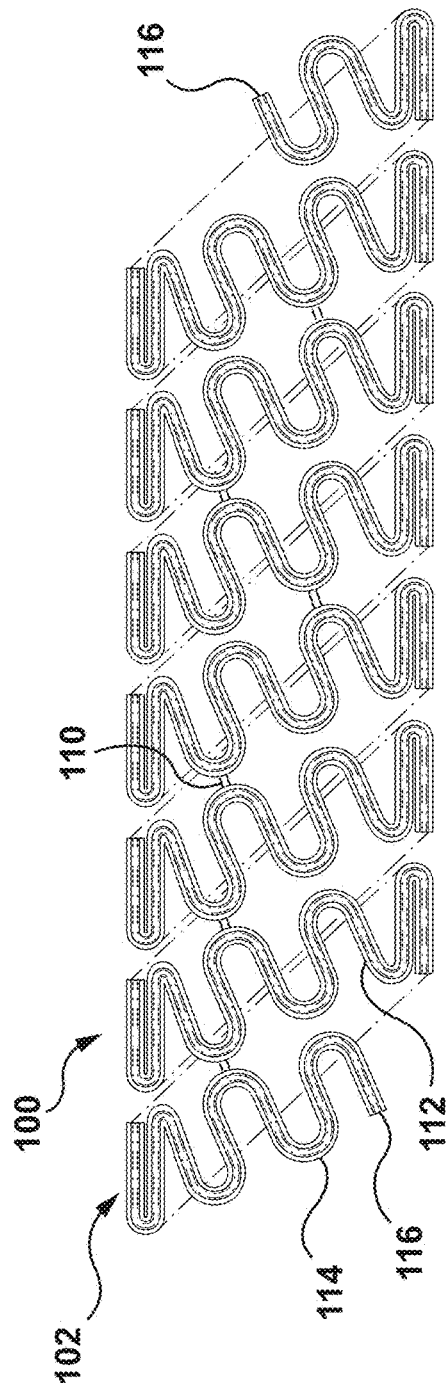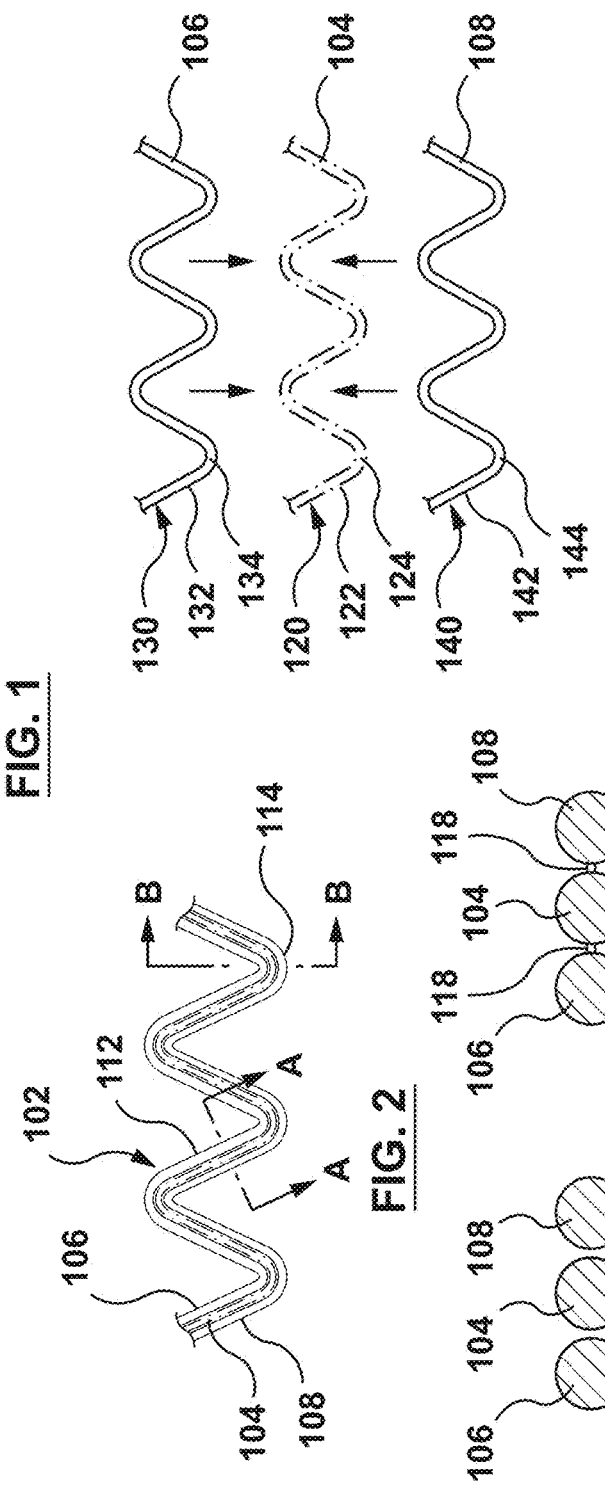

STENTS FORMED FROM DISSIMILAR METALS FOR TISSUE GROWTH CONTROL

CROSS REFERENCE TO RELATED APPLICATIONS

This application claims the benefit under 35 U.S.C. § 119(e) of the filing date of U.S. Provisional Application No. 62/420,478 filed Nov. 10, 2016, the contents of which are incorporated by reference herein, in their entirety.

FIELD OF THE INVENTION

The invention relates generally to medical devices, and more particularly to stents formed from dissimilar metals configured to control tissue growth.

BACKGROUND OF THE INVENTION

A wide range of medical treatments exist that utilize "endoluminal prostheses." As used herein, endoluminal prostheses is intended to cover medical devices that are adapted for temporary or permanent implantation within a body lumen, including both naturally occurring and artificially made lumens, such as without limitation: arteries, whether located within the coronary, mesentery, peripheral, or cerebral vasculature; veins; gastrointestinal tract; biliary tract; urethra; trachea; hepatic shunts; and fallopian tubes.

Accordingly, a wide assortment of endoluminal prostheses have been developed, each providing a uniquely beneficial structure to modify the mechanics of the targeted lumen wall. For example, stent prostheses are known for implantation within body lumens to provide artificial radial support to the wall tissue, which forms the various lumens within the body, and often more specifically, for implantation within the blood vessels of the body.

Essentially, stents that are presently utilized are made to be permanently or temporarily implanted. A stent is designed to be maintained in a body lumen for an indeterminate amount of time and is typically designed to provide long term support for damaged or traumatized wall tissues of the lumen. There are numerous conventional applications for permanent stents including cardiovascular, urological, gastrointestinal, and gynecological applications. However, stents, over time, may become encapsulated and covered with endothelium tissues, for example, in cardiovascular applications. There remains a need in the art for improvements relating to the control of tissue growth around stents.

BRIEF SUMMARY OF THE INVENTION

Embodiments hereof relate to stents configured to control tissue growth. In an embodiment, a stent includes a composite wire helically wound into a stent having a tubular configuration. The composite wire includes a first wire and a second wire coupled together, the first and second wires being formed from dissimilar metals such that a potential difference is formed when the dissimilar metals are exposed to bodily fluids. The potential difference is configured to inhibit cell proliferation and thereby control tissue growth around the stent after implantation.

In another embodiment, a stent includes a hollow composite wire helically wound into a stent having a tubular configuration, wherein the hollow composite wire includes an outer member, an inner member concentrically disposed within the outer member, a lumen extending longitudinally within the inner member, and a plurality of openings disposed through the outer member and the inner member to the lumen. The inner member includes a first longitudinal strip and a second longitudinal strip joined together, the first and second longitudinal strips being formed from dissimilar metals such that a potential difference is formed when the dissimilar metals are exposed to bodily fluids. The potential difference is configured to inhibit cell proliferation and thereby control tissue growth around the stent after implantation.

In another embodiment, a stent includes a composite wire helically wound into a stent having a tubular configuration. The composite wire includes a plurality of windows along a length of the composite wire. An insert is disposed within each window of the plurality of windows. The insert is formed from a dissimilar metal than the composite wire such that a potential difference is formed when the dissimilar metals are exposed to bodily fluids. The potential difference is configured to inhibit cell proliferation and thereby control tissue growth around the stent after implantation.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a schematic illustration of stent according to an embodiment hereof, wherein the stent is formed from a composite wire that includes a first wire, a second wire, and a third wire coupled together, the first, second, and third wires being nested within each other to form the composite wire.

FIG. 2 is an enlarged view of a portion of the composite wire of FIG. 1.

FIG. 2A is schematic cross-sectional view taken along line A-A of FIG. 1.

FIG. 2B is schematic cross-sectional view taken along line B-B of FIG. 1.

FIG. 3 is an exploded view of the portion of the composite wire of FIG. 2.

DETAILED DESCRIPTION OF THE INVENTION

Figure 4:
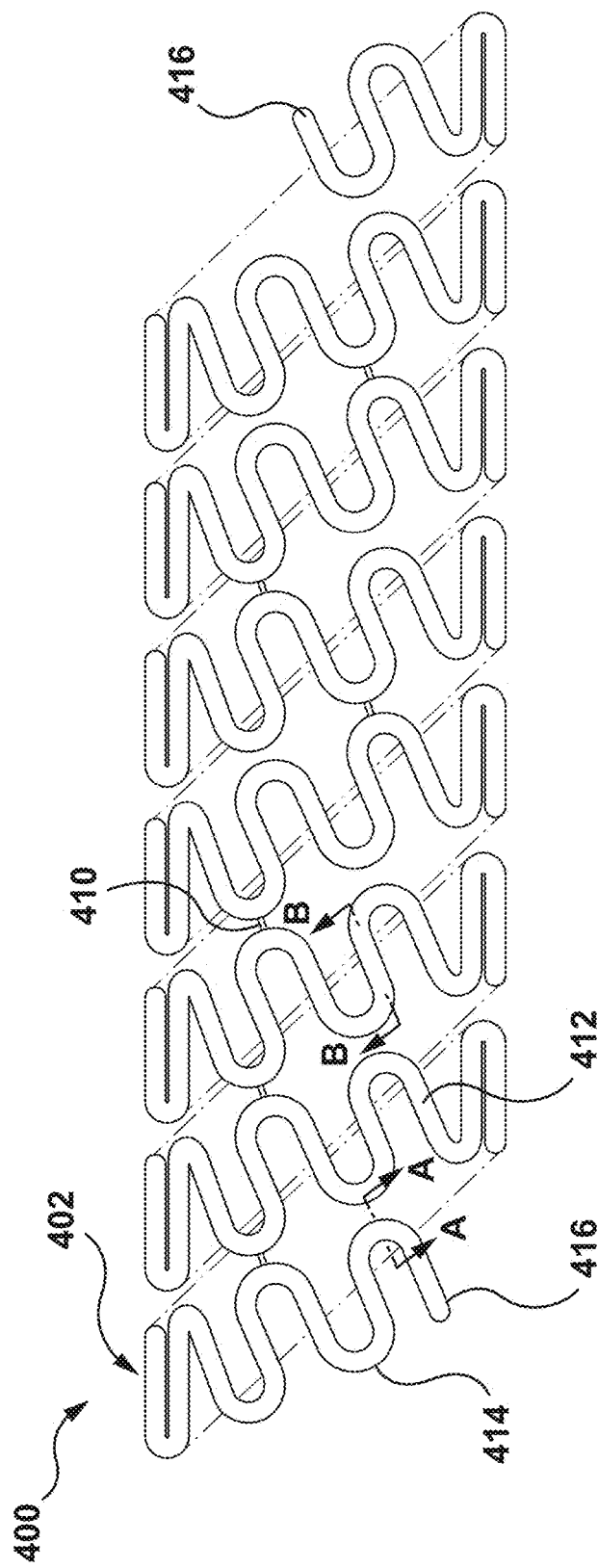
FIG. 4 is a schematic illustration of stent according to another embodiment hereof, wherein the stent is formed from a composite wire that includes a first wire, a second wire, and a third wire coupled together, the first, second, and third wires being stacked directly upon each other to form the composite wire.

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of the invention is in the context of treatment of blood vessels, the invention may also be used in any other body passageways where it is deemed useful. Furthermore, there is no intention to be bound by any expressed or implied theory presented in the preceding technical field, background, brief summary or the following detailed description.

FIG. 1 is a schematic illustration of a stent 100 according to an embodiment hereof, wherein the stent 100 is formed from a composite wire 102 that includes a first wire 104, a second wire 106, and a third wire 108 coupled together. In the embodiment of FIGS. 1-3, the first wire 104, the second wire 106, and the third wire 108 are nested within each other to form the composite wire 102 as will be explained in more detail herein. The term "wire" as used herein means an elongated element or filament and is not limited to a particular cross-sectional shape or material, unless so specified. Further, the term "composite wire" as used herein means two or more wires, i.e., elongated elements or filaments, coupled together along at least a portion thereof as described herein. Although each of the first wire 104, the second wire 106, and the third wire 108 is shown herein as having a generally circular cross-section, the first wire 104, the second wire 106, and/or the third wire 108 may be generally elliptical or rectangular in cross-section. Cross-sections having flat contact surfaces, such as but not limited to rectangular cross-sections, may be preferred in some embodiments in order to maximize the contact between the first wire 104, the second wire 106, and/or the third wire 108. In addition, although shown with the same size or dimension, the first wire 104, the second wire 106, and/or the third wire 108 may have different sizes or dimensions. Dimensions and/or cross-sections of each individual wire may be altered to adjust potential or mechanical properties of the composite wire 102.

The composite wire 102 is helically wound into the stent 100 such that the stent 100 has a tubular configuration. More particularly, with reference to FIG. 1, the composite wire 102 is formed into a series of generally sinusoidal waveforms including generally straight segments or struts 112 joined by bent segments or crowns 114 and the waveform is helically wound to form a generally tubular stent 100. In the embodiment shown in FIG. 1, selected crowns 114 of longitudinally adjacent sinusoids may be joined by, for example, fusion points 110. Further, ends 116 of composite wire 102 may be welded, crimped or otherwise connected to other portions of composite wire 102 such that the ends 116 are not free ends. Ends 116 may alternatively be provided as free ends, as shown in FIG. 1. The invention hereof is not limited to the pattern shown in FIG. 1. The composite wire 102 of the stent 100 can be formed into any pattern suitable for use as a stent. For example, and not by way of limitation, the composite wire 102 of the stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is herein incorporated by reference in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As previously stated and as best shown in FIGS. 2-3, the composite wire 102 of the stent 100 includes the first wire 104, the second wire 106, and the third wire 108 coupled together. FIG. 2 is an enlarged view of a portion of the composite wire 102, and FIG. 3 is an exploded view of the first wire 104, the second wire 106, and the third wire 108 of the composite wire of FIG. 2. In addition, FIG. 2A is schematic cross-sectional view taken along line A-A of FIG.

1, while FIG. 2B is schematic cross-sectional view taken along line B-B of FIG. 1. Each of the first wire 104, the second wire 106, and the third wire 108 is a wire shaped into a generally sinusoidal waveform including generally straight segments or struts joined by bent segments or crowns. More particularly, the first wire 104 is shaped into a first sinusoidal waveform 120 including generally straight segments or struts 122 joined by bent segments or crowns 124. Similarly, the second wire 106 is shaped into a second sinusoidal waveform 130 including generally straight segments or struts 132 joined by bent segments or crowns 134 and the third wire 108 is shaped into a third sinusoidal waveform 140 including generally straight segments or struts 142 joined by bent segments or crowns 144. First, second, and third sinusoidal waveform 120, 130, 140, respectively, are substantially similar in size and shape. More particularly, in this embodiment, the second waveform 130 is configured to nest within the first waveform 120 and the third waveform 140 is also configured to nest within the first waveform 120 as shown in FIG. 2. As used herein, "nest within" includes that the bent segments or crowns of a waveform fit within or follow the contour of the bent segments or crowns of an adjacent waveform and the straight segments or struts extend alongside or follow the contour of the straight segments or struts of an adjacent waveform.

When the first wire 104, the second wire 106, and the third wire 108 are nested within each other to form the composite wire 102, at least some of the bent segments or crowns 124 of the first waveform 120 are joined by, for example, fusion points 118 to the adjacent bent segments or crowns 134 of the second waveform 130 and at least some of the bent segments or crowns 124 of the first waveform 120 are joined by, for example, fusion points 118 to the adjacent bent segments or crowns 144 of the third waveform 140 as shown in the cross-sectional view of FIG. 2B which is taken at a bent segment or crown 114 of composite wire 102. Fusion points 118 may be formed by welding or other suitable connection methods known to one of ordinary skill in the art. In the embodiment of FIG. 1-3, at least some of the generally straight segments or struts 122 of the first waveform 120 are not joined to the adjacent generally straight segments or struts 132 of the second waveform 130 and at least some of the generally straight segments or struts 122 of the first waveform 120 are not joined to the adjacent generally straight segments or struts 142 of the third waveform 140 as shown in the cross-sectional view of FIG. 2A which is taken at a generally straight segment or strut 112 of composite wire 102. Thus, in an embodiment, adjacent generally straight segments or struts of each waveform extend alongside each other without being joined together while adjacent bent segments or crowns of each waveform are joined together by fusion points 118. However, in another embodiment, adjacent bent segments or crowns of each waveform extend alongside each other without being joined together while adjacent generally straight segments or struts of each waveform are joined together. In yet another embodiment, both adjacent generally straight segments or struts of each waveform are joined together and adjacent bent segments or crowns of each waveform are joined together such that the entire lengths of each waveforms are joined together.

Stent 100 is configured to control tissue growth of the tissue surrounding stent 100 after implantation. More particularly, the first wire 104, the second wire 106, and the third wire 108 are formed from dissimilar metals such that galvanic coupling takes place therebetween when exposed to bodily fluids. As used herein, "galvanic coupling" occurs when there is a potential difference that occurs between two unlike or dissimilar metals in the presence of an electrolytic solution. Induced electric fields or potential differences may modify normal cellular function by either promoting or inhibiting cell division. More particularly, induced electric fields or potential differences may modify the membrane potential of a cell, which then affects known regulators of the cell cycle. The materials of the first wire 104, the second wire 106, and the third wire 108 are selected such that a galvanic coupling occurs between adjacent wires and the galvanic coupling induces a voltage or potential difference which inhibits or controls cell proliferation. In the present embodiment, galvanic coupling occurs because there is a potential difference between the materials of the first wire 104 and the second wire 106, as well as a potential difference between the materials of the first wire 104 and the third wire 108, in the presence of bodily fluids when the stent 100 is deployed in a body lumen. In a galvanic couple, the higher corrosion-resistant or more noble metal turns cathodic, and may also be referred to as the cathode or less active material. The less corrosion-resistant or less noble metal becomes anodic, and may also be referred to as the anode or active material. Typically, the cathodic material undergoes little or no corrosion in a galvanic couple, while the anodic material undergoes corrosion. In an embodiment, depending on the material selection for the dissimilar materials, the corrosion of the anodic material results in the formation of a stable oxide layer on the anodic material and the stable oxide layer decreases the potential or current flow over time. In another embodiment, depending on the material selection for the dissimilar materials, the corrosion of the anodic material results in soluble products that are washed away and ultimately result in the complete degradation of the anodic material. The voltage or potential difference formed between the materials of the first wire 104 and the second wire 106, as well as between the materials of the first wire 104 and the third wire 108, inhibits cell proliferation and thereby controls or limits excessive tissue growth around the stent 100 after implantation. More particularly, the ratio of the surface areas exposed to the conductive electrolytic solution dictates the resulting voltage or potential difference and associated current. Depending upon the material selection for the dissimilar materials, as well as the ratio of the surface areas exposed to the conductive electrolytic solution, the amount of corrosion of the anodic material can be controlled as well as the duration for which the voltage or potential difference is present. For example, a larger voltage or potential difference would lead to a faster reaction, resulting in a more rapid formation of a stable oxide layer or the complete degradation of the anodic material. The duration of the reaction may be designed to be present during vessel healing and remodeling so that the voltage or potential difference inhibits cell proliferation and controls or limits excessive tissue growth around the stent 100 during this targeted time period. After the targeted time period has passed, the change in voltage or potential difference and mechanical properties due to the loss of the anodic material would be acceptable.

The amount or degree of potential difference formed between the materials of the first wire 104 and the second wire 106, as well as between the materials of the first wire 104 and the third wire 108, is determined by the difference in electrolytic potential between the dissimilar metals. The electrolytic difference can be measured by the difference in voltage potential between the materials, which may be measured against a Standard Hydrogen Electrode (SHE). The potential difference between an anode and a cathode can be measured by a voltage measuring device. The absolute potential of the anode and cathode cannot be measured directly. Defining a standard electrode, such as hydrogen, all other potential measurements can be made against this standard electrode. If the standard electrode potential is set to zero, the potential difference measured can be considered as the absolute potential. Accordingly, a metal's Standard Electrode Potential (SEP) is the potential difference measured between the metal and the Standard Hydrogen Electrode (SHE). Although the present application explains the electrolytic or potential difference with reference to a SHE, the SHE is a reference selected for convenience because most available literature includes lists on the subject of potential differences with respect to the SHE. Of course, lists also exist with potential differences compared to other standard electrodes, such as, for example, gold. In an embodiment, the potential difference formed between the materials of the first wire 104 and the second wire 106, as well as between the materials of the first wire 104 and the third wire 108, is on the order of several hundred mV and is similar to a cell's membrane potential. This potential difference that is formed between the materials of the first wire 104 and the second wire 106, as well as between the materials of the first wire 104 and the third wire 108, creates electric fields which then inhibit cell proliferation. As such, in embodiments hereof, cell growth may be controlled by a potential difference driven by dissimilar metals. Such control of cell growth may eliminate the need for a drug coating on stent 100, although in other embodiments hereof a drug coating for additional or further control of tissue growth may be utilized on stent 100.

In an embodiment, the first wire 104 is made from tantalum. Tantalum in some literature is identified as having a Standard Electrode Potential of −0.60 Volts. In other embodiments, materials such as tungsten (SEP≈−0.58) may be used for the first wire 104. In another embodiment, the first wire 104 may be made of platinum or a platinum-iridium alloy. Platinum in some literature is identified as having a Standard Electrode Potential of about 1.188 Volts. In another embodiment, the first wire 104 may be made of gold. Gold in some literature is identified as having a Standard Electrode Potential of about 1.52 Volts. These SEP values depend on various measurement factors and conditions which could affect the values and are being used herein only to show exemplary SEP differences between materials described herein.

In an embodiment, the second wire 106 and the third wire 108 are each made of a cobalt-chromium alloy. As used herein, the term "cobalt-chromium" alloy includes alloys with cobalt and chromium. Generally, materials such as, but not limited to, cobalt-nickel-chromium alloys ("MP35N" and "MP20N") and chromium-nickel-tungsten-cobalt alloys ("L605") and cobalt-chromium-nickel-molybdenum alloys ("ELGILOY") are the types of materials included in the term "cobalt-chromium alloys" as used herein. A cobalt-chromium alloy in some literature is identified as having a Standard. Electrode Potential of about −0.25 Volts. In another embodiment, the second wire 106 and the third wire 108 are each made of magnesium or a magnesium alloy. Magnesium and magnesium alloys are also known to be bioabsorbable. Magnesium in some literature is identified as having a Standard Electrode Potential of about −2.37 Volts. In another embodiment, the second wire 106 and the third wire 108 are each made of zinc. Zinc in some literature is identified as having a Standard Electrode Potential of about −0.76 Volts. These SEP values depend on various measurement factors and conditions which could affect the value and is used herein only to show exemplary SEP differences between the materials described herein. Although described herein as being formed from the same relatively less noble material, in another embodiment hereof the second wire 106 and the third wire 108 may be formed from different materials, each of which is relatively less noble than the first wire 104.

In the embodiment described above, each of the second wire 106 and the third wire 108 is less noble (more active) than the first wire 104. Otherwise stated, a most/more noble and non-active material such as platinum or tantalum is selected for the first wire 104 (the cathode) and a least/less noble and active material such as a cobalt-chromium alloy or magnesium is selected for the second wire 106 and the third wire 108 (the anodes). The first wire 104 is sandwiched between the second wire 106 and the third wire 108, and thus the first wire 104 is in contact with each of the second wire 106 and the third wire 108. Thus, each of the second wire 106 and the third wire 108 acts as an anode and experiences galvanic coupling as a result of its contact with the first wire 104 made from a more noble material. A potential difference is formed between the more noble material of the first wire 104 and the less noble material of the second wire 106, as well as between the more noble material of the first wire 104 and the less noble material of the third wire 108, and the formed or induced potential differences inhibit cell proliferation and thereby control or limit excessive tissue growth around the stent 100 after implantation. More particularly, cells attach or couple to the outer surfaces of the first wire 104, the second wire 106, and the third wire 108. Once attached thereto, the cells grow or colonize and form an extracellular matrix around the outer surfaces of the first wire 104, the second wire 106, and the third wire 108 to couple the stent 100 to the vessel. The mechanical integration, or coupling of the stent 100 to the vessel may offer clinical benefit in reducing micro-damage to the tissue surrounding the stent 100 during biomechanical motion of the vessel, such as the repetitive constriction and dilation of the vessel due to cardiac pressure differentials of the cardiac cycle. The term "micro-damage," as used herein, means tissue damage due to the relative movement between a generally rigid stent and a generally flexible vessel. Further, the term "biomechanical motion," as used herein means the motion or movement of a vessel. For example, and not by way of limitation, biomechanical motion includes the repetitive constriction and dilation of a body vessel due to cardiac pressure differentials of the cardiac cycle. However, excessive tissue growth and restenosis is avoided due to the potential differences formed between the dissimilar metals of the first wire 104, the second wire 106, and the third wire 108.

FIG. 4 is a schematic illustration of a stent 400 according to another embodiment hereof, wherein the stent 400 is formed from a composite wire 402 that includes a first wire 404, a second wire 406, and a third wire 408 coupled together. In the embodiment of FIGS. 1-3, the first wire 104, the second wire 106, and the third wire 108 are directly beside each other, i.e., in a circumferential direction after stent 100 is formed, to form the composite wire 102. However, in the embodiment of FIGS. 4-4B, the first wire 404, the second wire 406, and the third wire 408 are directly stacked on top of each other, i.e., in a radial direction after stent 400 is formed, to form the composite wire 402. Although each of the first wire 404, the second wire 406, and the third wire 408 is shown herein as generally having a circular cross-section, first wire 404, the second wire 406, and/or the third wire 408 may be generally elliptical or rectangular in cross-section. Similar to composite wire 102, the composite wire 402 is helically wound into the stent 400 such that the stent 400 has a tubular configuration as shown in FIG. 4. More particularly, the composite wire 402 is formed into a series of generally sinusoidal waveforms including generally straight segments or struts 412 joined by bent segments or crowns 414 and the waveform is helically wound to form a generally tubular stent 400. In the embodiment shown in FIG. 4, selected crowns 414 of longitudinally adjacent sinusoids may be joined by, for example, fusion points 410. Further, ends 416 of composite wire 402 may be welded, crimped or otherwise connected to other portions of composite wire 402 such that the ends 416 are not free ends. Ends 416 may alternatively be provided as free ends, as shown in FIG. 4. The invention hereof is not limited to the pattern shown in FIG. 4. The composite wire 402 of the stent 400 can be formed into any pattern suitable for use as a stent. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

Figure 4B:
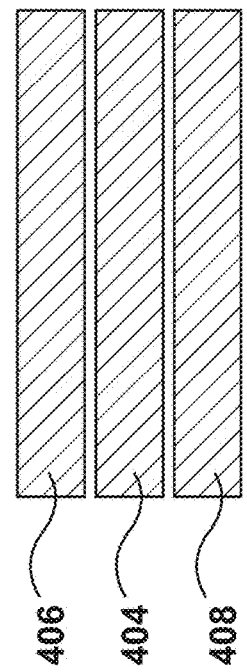
FIG. 4B is schematic sectional view taken along line B-B of FIG. 4.
Figure 4A:
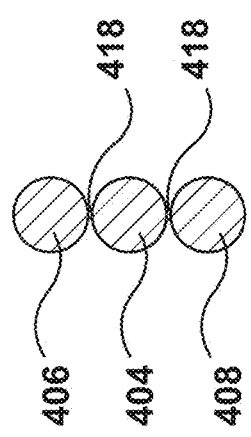
FIG. 4A is schematic cross-sectional view taken along line A-A of FIG. 4.

As previously stated and as best shown in FIGS. 4A-4B, the composite wire 402 of the stent 400 includes the first wire 404, the second wire 406, and the third wire 408 coupled together. FIG. 4A is schematic cross-sectional view taken along line A-A of FIG. 4, while FIG. 4B is schematic sectional view taken along line B-B of FIG. 4. Similar to the first wire 104, the second wire 106, and the third wire 108, each of the first wire 404, the second wire 406, and the third wire 408 is a wire shaped into a generally sinusoidal waveform including generally straight segments or struts joined by bent segments or crowns. The waveforms of the first wire 404, the second wire 406, and the third wire 408 are substantially similar in size and shape and are stacked, piled, or otherwise disposed directly on top of each other with the first wire 404 being sandwiched or disposed between the second wire 406 and the third wire 408.

When the first wire 404, the second wire 406, and the third wire 408 are stacked on top of each other to form the composite wire 402, at least some of the bent segments or crowns of the first waveform of the first wire 404 are joined by, for example, fusion points 418 to the adjacent bent segments or crowns of the second waveform of the second wire 406 and at least some of the bent segments or crowns of the first waveform of the first wire 404 are joined by, for example, fusion points 418 to the adjacent bent segments or crowns of the third waveform of the third wire 408 as shown in the cross-sectional view of FIG. 4A which is taken at a bent segment or crown 414 of composite wire 402. Fusion points 418 may be formed by welding or other suitable connection methods known to one of ordinary skill in the art. In the embodiment of FIG. 4-4B, at least some of the generally straight segments or struts of the first waveform of the first wire 404 are not joined to the adjacent generally straight segments or struts of the second waveform of the second wire 406 and at least some of the generally straight segments or struts of the first waveform of the first wire 404 are not joined to the adjacent generally straight segments or struts of the third waveform of the third wire 408 as shown in the sectional view of FIG. 4B which is taken at a generally straight segment or strut 412 of composite wire 402. Thus, in an embodiment, adjacent generally straight segments or struts of each waveform extend alongside each other without being joined together while adjacent bent segments or crowns of each waveform are joined together by fusion points 418. However, in another embodiment, adjacent bent segments or crowns of each waveform extend alongside each other without being joined together while adjacent generally straight segments or struts of each waveform are joined together. In yet another embodiment, both adjacent generally straight segments or struts of each waveform are joined together and adjacent bent segments or crowns of each waveform are joined together such that the entire lengths of each waveforms are joined together.

Similar to stent 100, stent 400 is configured to control tissue growth of the tissue surrounding stent 400 after implantation. More particularly, the first wire 404 is formed from the same material as the first wire 104, the second wire 406 is formed from the same material as the second wire 106, and the third wire 408 is formed from the same material as the third wire 108. As such, the first wire 404, the second wire 406, and the third wire 408 are formed from dissimilar metals such that galvanic coupling takes place therebetween when exposed to bodily fluids and the galvanic coupling induces a voltage or potential difference which inhibits or controls cell proliferation as described above.

Figure 5:
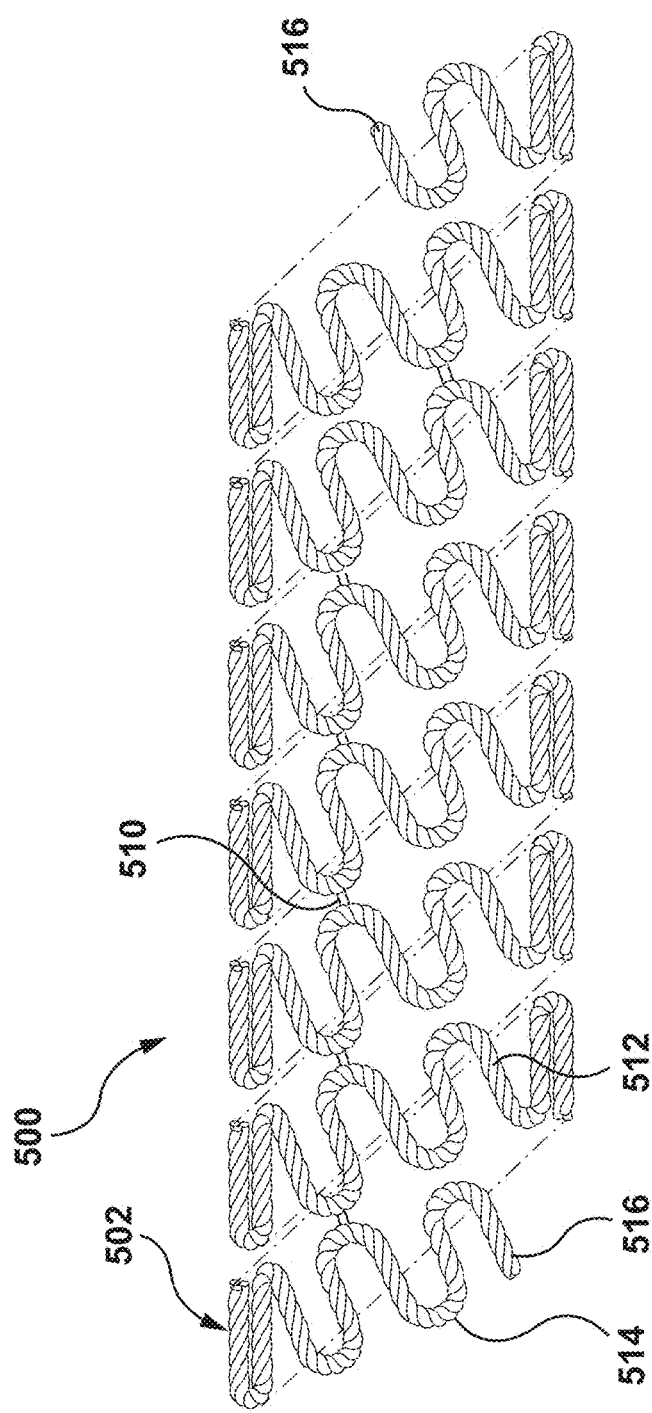
FIG. 5 is a schematic illustration of stent according to another embodiment hereof, wherein the stent is formed from a composite wire that includes a first wire, a second wire, and a third wire coupled together, the first, second, and third wires being twisted together to form the composite wire.
Figure 5A:
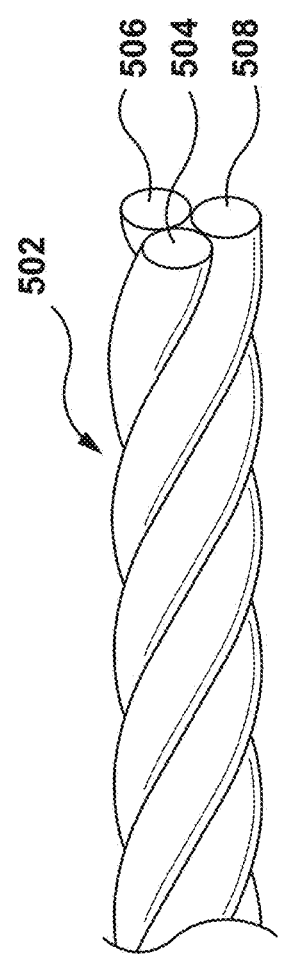
FIG. 5A is an enlarged view of a portion of the composite wire of FIG. 5.

FIG. 5 is a schematic illustration of a stent 500 according to another embodiment hereof, wherein the stent 500 is formed from a composite wire 502 that includes a first wire 504, a second wire 506, and a third wire 508 coupled together. Although each of the first wire 504, the second wire 506, and the third wire 508 is shown herein as generally having a circular cross-section, first wire 504, the second wire 506, and/or the third wire 508 may be generally elliptical or rectangular in cross-section. FIG. 5A is an enlarged view of a portion of the composite wire 502. The first wire 504, the second wire 506, and the third wire 508 are twisted, woven, or otherwise intertwined together to form the composite wire 502 as best shown in FIG. 5A. Composite wire 502 is then helically wound into the stent 500 such that the stent 500 has a tubular configuration as shown in FIG. 5. More particularly, the composite wire 502 is formed into a series of generally sinusoidal waveforms including generally straight segments or struts 512 joined by bent segments or crowns 514 and the waveform is helically wound to form a generally tubular stent 500. In the embodiment shown in FIG. 5, selected crowns 514 of longitudinally adjacent sinusoids may be joined by, for example, fusion points 510. Further, ends 516 of composite wire 502 may be welded, crimped or otherwise connected to other portions of composite wire 502 such that the ends 516 are not free ends. Ends 516 may alternatively be provided as free ends, as shown in FIG. 5. The invention hereof is not limited to the pattern shown in FIG. 5. The composite wire 502 of the stent 500 can be formed into any pattern suitable for use as a stent. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

Similar to stent 100, stent 500 is configured to control tissue growth of the tissue surrounding stent 500 after implantation. More particularly, the first wire 504 is formed from the same material as the first wire 104, the second wire 506 is formed from the same material as the second wire 106, and the third wire 508 is formed from the same material as the third wire 108. As such, the first wire 504, the second wire 506, and the third wire 508 are formed from dissimilar metals such that galvanic coupling takes place therebetween when exposed to bodily fluids and the galvanic coupling induces a voltage or potential difference which inhibits or controls cell proliferation as described above.

Figure 6:
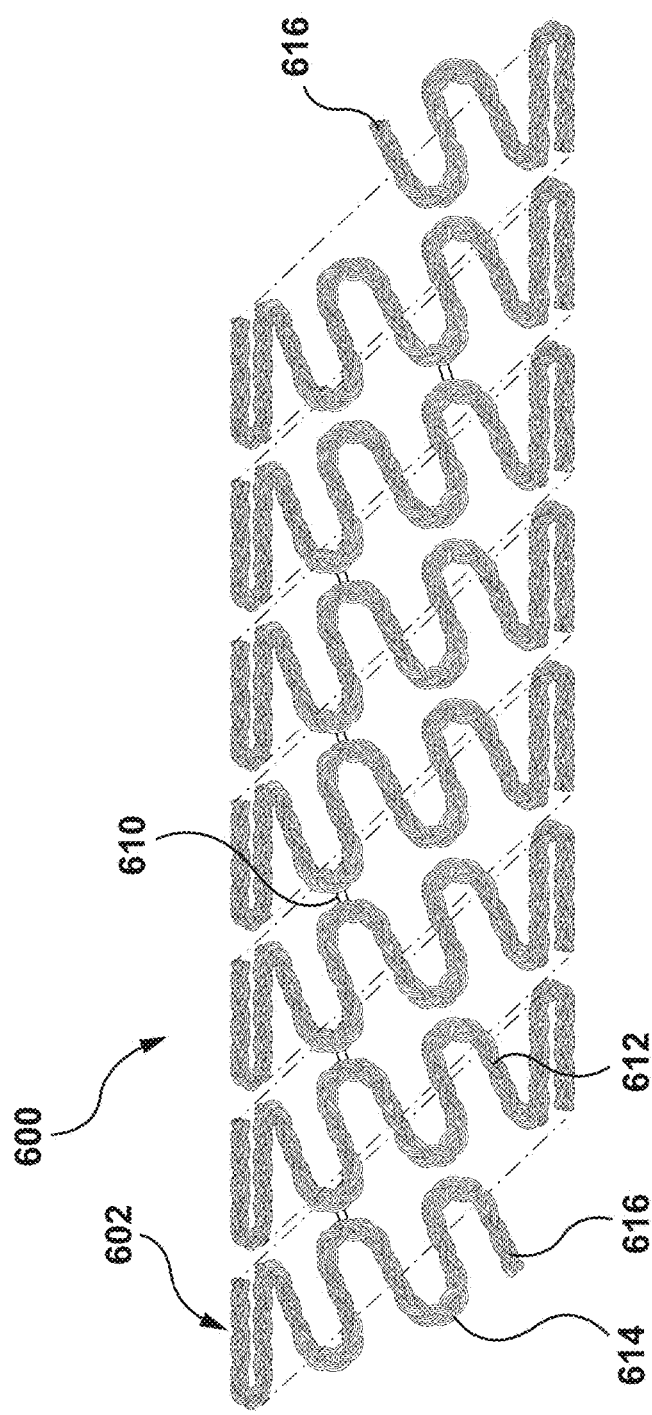
FIG. 6 is a schematic illustration of stent according to another embodiment hereof, wherein the stent is formed from a composite wire that includes a first wire, a second wire, and a third wire coupled together, the first, second, and third wires being braided together to form the composite wire.
Figure 6A:
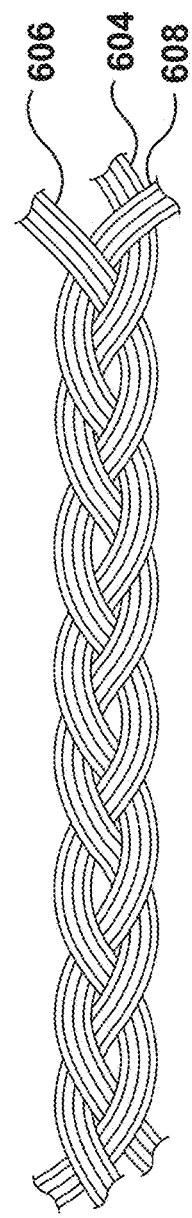
FIG. 6A is an enlarged view of a portion of the composite wire of FIG. 6.

FIG. 6 is a schematic illustration of a stent 600 according to another embodiment hereof, wherein the stent 600 is formed from a composite wire 602 that includes a first wire 604, a second wire 606, and a third wire 608 coupled together. Although each of first wire 604, the second wire 606, and the third wire 608 is shown herein as generally having a circular cross-section, first wire 604, the second wire 606, and/or the third wire 608 may be generally elliptical or rectangular in cross-section. FIG. 6A is an enlarged view of a portion of the composite wire 602. The first wire 604, the second wire 606, and the third wire 608 are braided together to form the composite wire 602 as best shown in FIG. 6A. Composite wire 602 is then helically wound into the stent 600 such that the stent 600 has a tubular configuration as shown in FIG. 6. More particularly, the composite wire 602 is formed into a series of generally sinusoidal waveforms including generally straight segments or struts 612 joined by bent segments or crowns 614 and the waveform is helically wound to form a generally tubular stent 600. In the embodiment shown in FIG. 6, selected crowns 614 of longitudinally adjacent sinusoids may be joined by, for example, fusion points 610. Further, ends 616 of composite wire 602 may be welded, crimped or otherwise connected to other portions of composite wire 602 such that the ends 616 are not free ends. Ends 616 may alternatively be provided as free ends, as shown in FIG. 6. The invention hereof is not limited to the pattern shown in FIG. 6. The composite wire 602 of the stent 600 can be formed into any pattern suitable for use as a stent. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

Similar to stent 100, stent 600 is configured to control tissue growth of the tissue surrounding stent 600 after implantation. More particularly, the first wire 604 is formed from the same material as the first wire 104, the second wire 606 is formed from the same material as the second wire 106, and the third wire 608 is formed from the same material as the third wire 108. As such, the first wire 604, the second wire 606, and the third wire 608 are formed from dissimilar metals such that galvanic coupling takes place therebetween when exposed to bodily fluids and the galvanic coupling induces a voltage or potential difference which inhibits or controls cell proliferation as described above.

Figure 7:
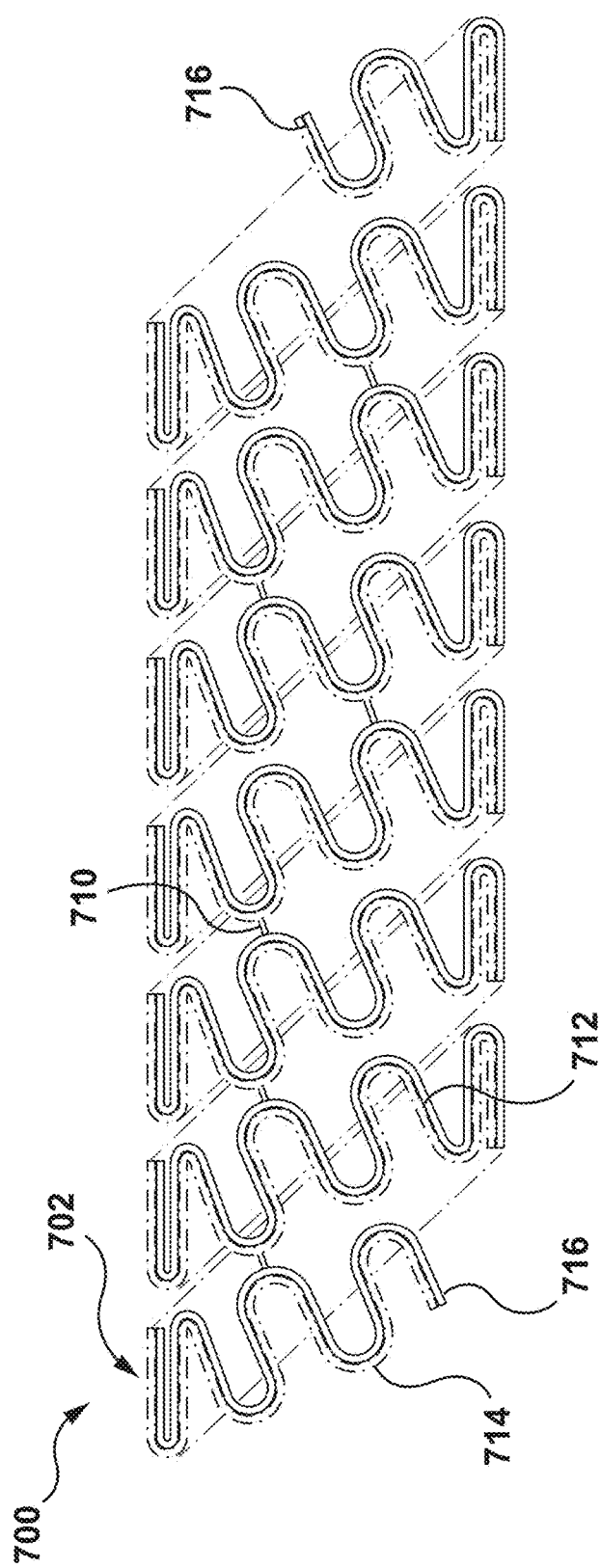
FIG. 7 is a schematic illustration of stent according to another embodiment hereof, wherein the stent is formed from a composite wire that includes a first wire and a second wire coupled together, the first and second wires being nested within each other to form the composite wire.
Figure 7A:
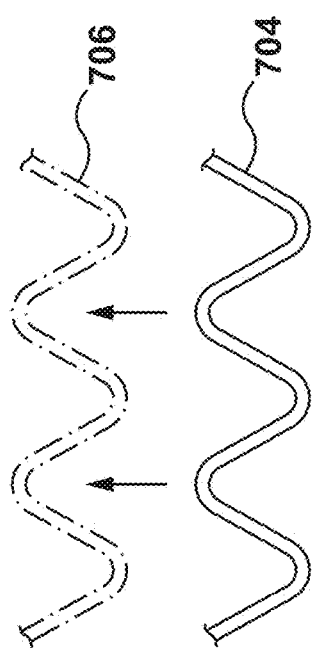
FIG. 7A is an enlarged view of a portion of the composite wire of FIG. 7.
Figure 8:
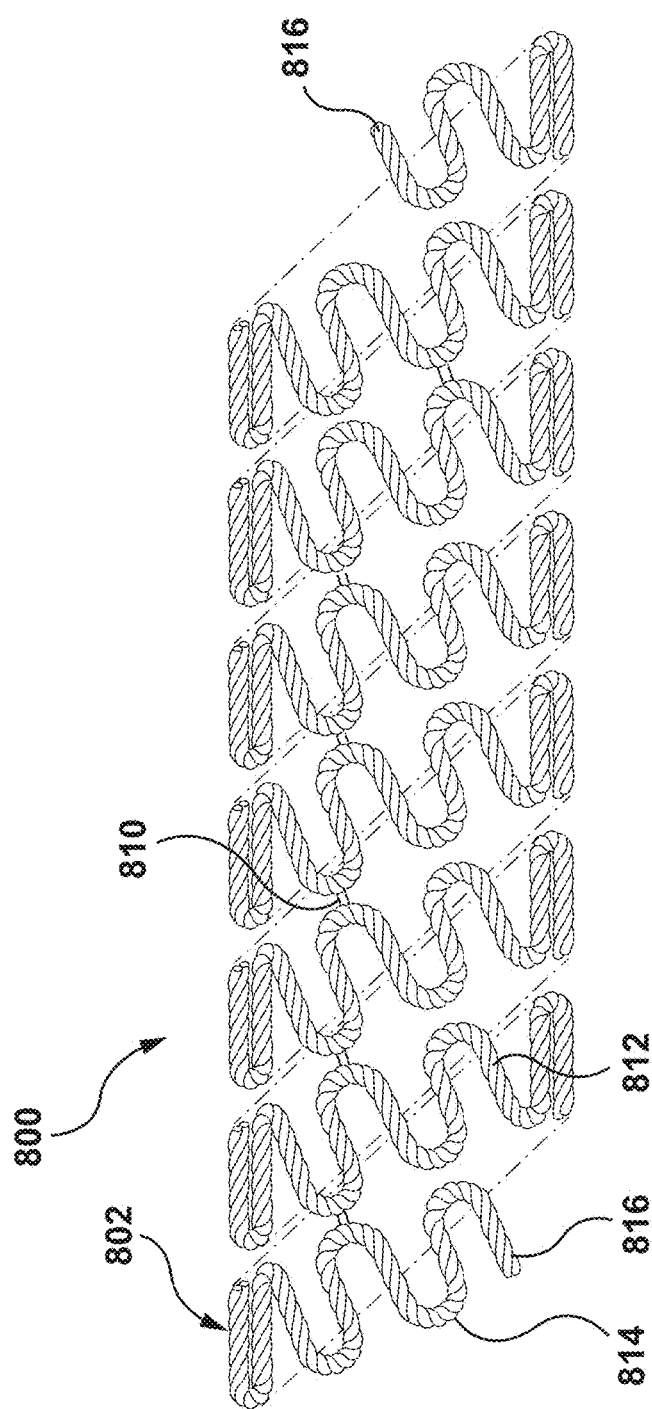
FIG. 8 is a schematic illustration of stent according to another embodiment hereof, wherein the stent is formed from a composite wire that includes a first wire and a second wire coupled together, the first and second wires being twisted together to form the composite wire.
Figure 8A:
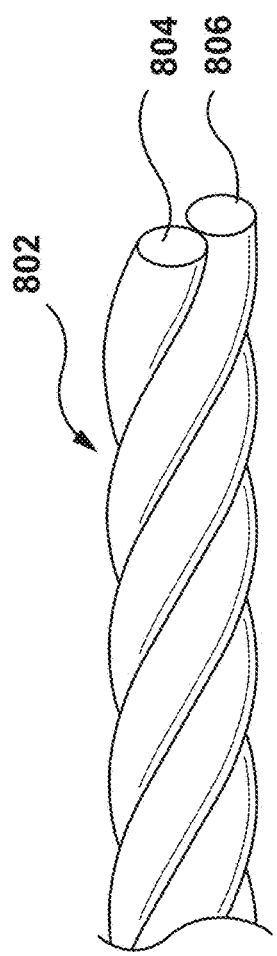
FIG. 8A is an enlarged view of a portion of the composite wire of FIG. 8.

Although the above embodiments illustrate composite wires being formed from three wires of dissimilar metals, it will be understood by one of ordinary skill in the art that a greater number or a fewer number of wires may be used to form a composite wire. A minimum of two wires of dissimilar metals are required such that galvanic coupling takes place therebetween when exposed to bodily fluids and the galvanic coupling induces a voltage or potential difference which inhibits or controls cell proliferation as described above. When a third wire is utilized in the composite wire as shown in embodiments described above, the third wire may be configured to enhance mechanical performance of the composite wire or may be configured to modify the ratio between dissimilar metals and the associated or resulting potential. FIG. 7 is a schematic illustration of a stent 700 according to another embodiment hereof, wherein the stent 700 is formed from a composite wire 702 that includes a first wire 704 and a second wire 706 coupled together. FIG. 7A is an enlarged exploded view of a portion of the composite wire 702. The first wire 704 is similar to the first wire 104 described above, and the second wire 706 is similar to the second wire 106 described above such that the generally sinusoidal waveform of the second wire 706 is configured to nest within the generally sinusoidal waveform of the first wire 704. Similarly, FIG. 8 is a schematic illustration of a stent 800 according to another embodiment hereof, wherein the stent 800 is formed from a composite wire 802 that includes a first wire 804 and a second wire 806 coupled together. FIG. 8A is an enlarged view of a portion of the composite wire 802. The first wire 804 is similar to the first wire 504 described above, and the second wire 806 is similar to the second wire 506 described above such that the first wire 804 and the second wire 806 are twisted, woven, or otherwise intertwined together to form the composite wire 802 as best shown in FIG. 8A. Alternatively, in another embodiment hereof, composite wire 802 may be formed by positioning a helical groove around the first wire 804 and depositing the second wire 806 therein. Regardless of how composite wire 802 is formed, composite wire 802 is then helically wound into the stent 800 such that the stent 800 has a tubular configuration as shown in FIG. 8. Each of stents 700, 800 is configured to control tissue growth of the tissue surrounding stents 700, 800 after implantation. More particularly, the first wires 704, 804 are formed from the same material as the first wire 104 and the second wires 706, 806 are formed from the same material as the second wire 106. As such, the first wires 704, 804 and the second wires 706, 806, respectively, are formed from dissimilar metals such that galvanic coupling takes place therebetween when exposed to bodily fluids and the galvanic coupling induces a voltage or potential difference which inhibits or controls cell proliferation as described above.

Figure 9:
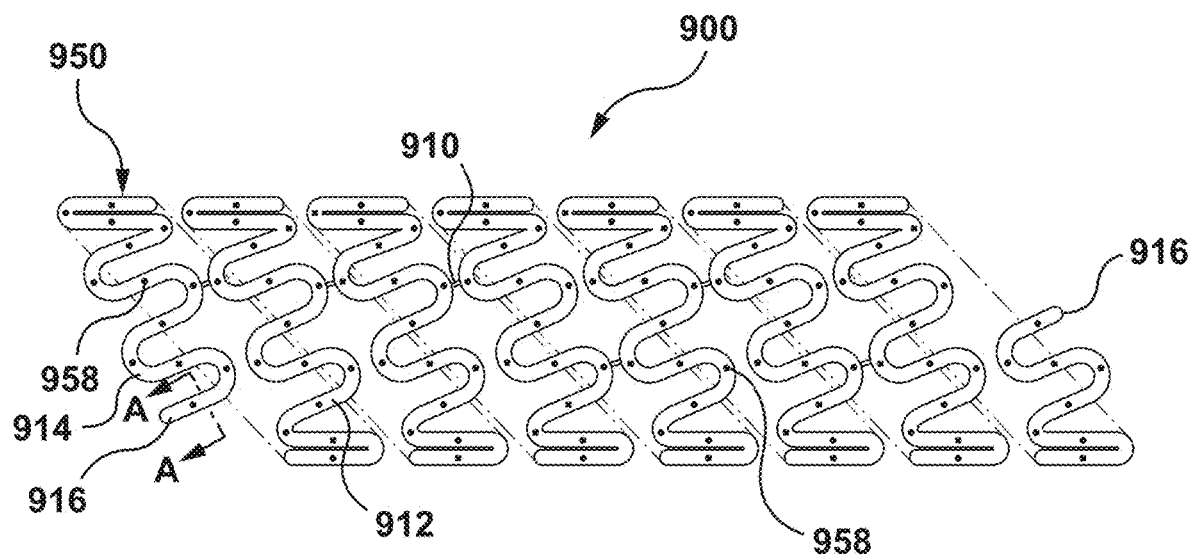
FIG. 9 is a schematic illustration of stent according to another embodiment hereof, wherein the stent is formed from a hollow composite wire that includes an inner member having a first longitudinal strip, a second longitudinal strip, a third longitudinal strip, and a fourth longitudinal strip joined together.
Figure 9A:
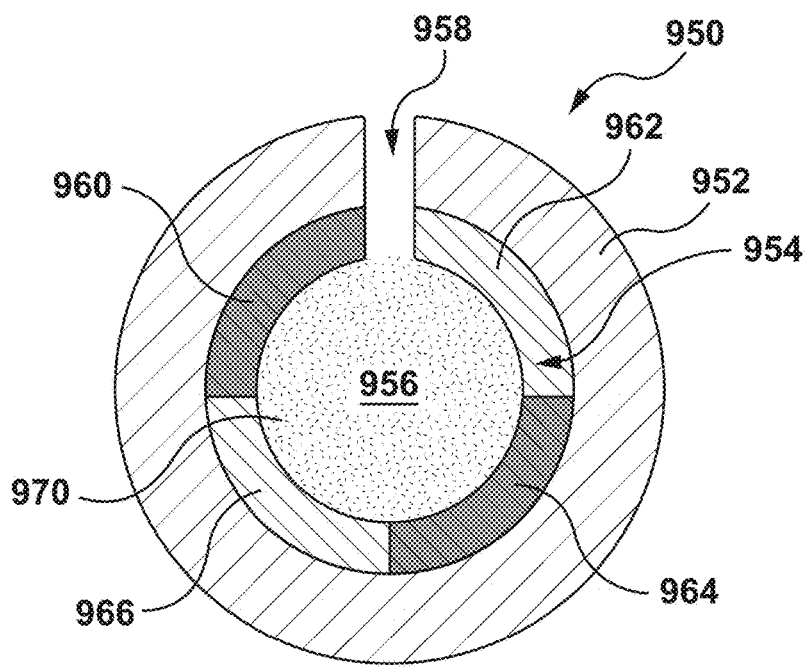
FIG. 9A is schematic cross-sectional view taken along line A-A of FIG. 9.

FIG. 9 is a schematic illustration of a stent 900 according to another embodiment hereof. FIG. 9A is schematic cross-sectional view taken along line A-A of FIG. 9. The stent 900 is formed from a hollow composite wire 950 that includes an outer member 952, an inner member 954 concentrically disposed within the outer member 952, and a lumen 956 extending longitudinally within the inner member 954. The hollow composite wire 950 further includes a plurality of openings 958 disposed through the outer member 952 and the inner member 954 to the lumen 956. The outer member 952 may be any material that is suitable to be used as a stent. For example, and not by way of limitation, the outer member 952 may be a cobalt-chromium alloy. As will be explained in more detail herein, the inner member 954 has a first longitudinal ribbon or strip 960, a second longitudinal ribbon or strip 962, a third longitudinal ribbon or strip 964, and a fourth longitudinal ribbon or strip 966 joined together. In an embodiment, each of the first longitudinal strip 960, the second longitudinal strip 962, the third longitudinal strip 964, and the fourth longitudinal strip 966 extends a full length of the hollow composite wire 950. Composite wire 902 is helically wound into the stent 900 such that the stent 900 has a tubular configuration as shown in FIG. 9. More particularly, the composite wire 902 is formed into a series of generally sinusoidal waveforms including generally straight segments or struts 912 joined by bent segments or crowns 914 and the waveform is helically wound to form a generally tubular stent 900. In the embodiment shown in FIG. 9, selected crowns 914 of longitudinally adjacent sinusoids may be joined by, for example, fusion points 910. Further, ends 916 of composite wire 902 may be welded, crimped or otherwise connected to other portions of composite wire 902 such that the ends 916 are not free ends. Ends 916 may alternatively be provided as free ends, as shown in FIG. 9. The invention hereof is not limited to the pattern shown in FIG. 9. The composite wire 902 of the stent 900 can be formed into any pattern suitable for use as a stent. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

In the embodiment of FIGS. 9-9A, a biologically or pharmacologically active agent 970 (hereafter referred to as "active agent 970" for simplicity) is deposited within the lumen 956 of the hollow composite wire 950 as shown in FIG. 9A. The plurality of openings 958 provide access to the lumen 956 to permit the active agent 970 to be released from the lumen 956. Further, the plurality of openings 958 provide access to the lumen 956 to permit tissue growth into the lumen 956 after the active agent 970 has been released from the lumen 956 and to permit bodily fluids to reach the inner member 954 such that galvanic coupling can begin between the first longitudinal strip 960, the second longitudinal strip 962, the third longitudinal strip 964, and the fourth longitudinal strip 966 as will be described in more detail herein. Openings 958 may be laser drilled into hollow composite wire 950 or formed by other methods. The plurality of openings 958 may be sized and shaped as desired to control both the elution rate of the active agent 970 from the lumen 956 and to control the growth of cells into the lumen 956 of the stent 900. Larger sized openings 958 generally permit a faster elution rate and a faster growth rate and smaller sized openings 958 generally provide a slower elution rate and a slower growth rate. The size and/or quantity of the plurality of openings 958 may be varied along the stent 900 in order to vary both the quantity and/or rate of the active agent 970 being eluted from stent 900 and the growth of cells into the lumen 956 at different portions of stent 900. The plurality of openings 958 may be, for example and not by way of limitation, 10-30 µm in diameter. While shown in FIG. 9 with the plurality of openings 958 on an outwardly facing or abluminal surface, this is by way of example and not limitation, and the plurality of openings 958 may be provided on the abluminal surface and/or on an inward facing or luminal surface, or may be provided anywhere along the circumference of the hollow composite wire 950.

As used herein, a biologically or pharmacologically "active agent" may include, but is not limited to, antineoplastic, antimitotic, anti-inflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other active substances or agents that may be used include nitric oxide, alpha-interferon, genetically engineered epithelial cells, and dexamethasone. In other examples, the active substance is a radioactive isotope for implantable device usage in radioactive procedures. Examples of radioactive isotopes include, but are not limited to, phosphorus ($P^{32}$), palladium ($Pd^{103}$), cesium ($Cs^{131}$), Iridium (V') and iodine ($I^{125}$). While the preventative and treatment properties of the foregoing active substances or agents are well-known to those of ordinary skill in the art, the substances or agents are provided by way of example and are not meant to be limiting. Other active substances are equally applicable for use with the disclosed methods and compositions. Further, a carrier may be used with the biologically or pharmacologically active agent. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the drug and the solvent to aid elution of the drug.

While described herein with the active agent 970 within the lumen 956, this is not meant to be limiting, and in an alternative embodiment, the lumen 956 may not contain the active agent 970. When the active agent 970 is not utilized, the plurality of openings 958 provide access to the lumen 956 only to permit tissue growth into the lumen 956 and to permit bodily fluids to reach the inner member 954 such that galvanic coupling can begin between the first longitudinal strip 960, the second longitudinal strip 962, the third longitudinal strip 964, and the fourth longitudinal strip 966 as will be described in more detail herein.

The ends 916 of the hollow composite wire 950 may be closed by crimping excess material of the hollow composite wire 950 to close the lumen 956. In the embodiment of FIG. 9, with the active agent 970 disposed within the lumen 956, closing the ends 916 prevents the active agent 970 from prematurely releasing from the ends 916. However, closing the ends 916 is not required as the active agent 970 may be dried, provided within a polymer matrix, enclosed within a liner (not shown in FIG. 9A), or otherwise protected from premature release from the ends 916. Further, the ends 916 may be welded, crimped or otherwise connected to other portions of the hollow composite wire 950 such that the ends 916 are not free ends.

Stent 900 is configured to control tissue growth of the tissue surrounding stent 900 after implantation. More particularly, the first longitudinal strip 960, the second longitudinal strip 962, the third longitudinal strip 964, and the fourth longitudinal strip 966 are formed from dissimilar metals such that galvanic coupling takes place therebetween when exposed to bodily fluids. The materials of the first longitudinal strip 960, the second longitudinal strip 962, the third longitudinal strip 964, and the fourth longitudinal strip 966 are selected such that galvanic coupling occurs between adjacent strips and the galvanic coupling induces a voltage or potential difference which inhibits or controls cell proliferation. In an embodiment, the first longitudinal strip 960 and the third longitudinal strip 964 are each made from a relatively more noble material such as platinum, a platinum-iridium alloy, tantalum, tungsten, or gold. In an embodiment, the second longitudinal strip 962 and the fourth longitudinal strip 966 are each made of a relatively less noble material such as a cobalt-chromium alloy, magnesium, or zinc.

In the embodiment described above, each of the second longitudinal strip 962 and the fourth longitudinal strip 966 is less noble (more active) than each of the first longitudinal strip 960 and the third longitudinal strip 964 made from a more noble material. Each of the first longitudinal strip 960 and the third longitudinal strip 964 is sandwiched or disposed between the second longitudinal strip 962 and the fourth longitudinal strip 966, and thus each of the first longitudinal strip 960 and the third longitudinal strip 964 is in contact with each of the second longitudinal strip 962 and the fourth longitudinal strip 966. Thus, each of the second longitudinal strip 962 and the fourth longitudinal strip 966 acts as an anode and experiences galvanic coupling as a result of its contact with the first longitudinal strip 960 and the third longitudinal strip 964 made from a more noble material. A potential difference is formed between the more noble material of the first longitudinal strip 960 and the third longitudinal strip 964 and the less noble material of the second longitudinal strip 962 and the fourth longitudinal strip 966, and the formed or induced potential differences inhibits cell proliferation and thereby controls or limits excessive tissue growth around the stent 900 after implantation. More particularly, when the stent 900 is deployed within a vessel, the active agent 970 elutes from the lumen 956 of the stent 900. Once the active agent 970 has been eluted, cells originating from the vessel migrate through the plurality of openings 958 and into the lumen 956. The cells attach or couple to surfaces within the lumen 956. More specifically, the cells couple to the inner surface of the inner member 954. Once attached thereto, the cells grow or colonize and form an extracellular matrix on the inner surface of the inner member 954 to couple the stent 900 to the vessel. The mechanical integration, or coupling of the stent 900 to the vessel may offer clinical benefit in reducing micro-damage to the tissue surrounding the stent 900 during biomechanical motion of the vessel, such as the repetitive constriction and dilation of the vessel due to cardiac pressure differentials of the cardiac cycle. However, excessive tissue growth and restenosis is avoided due to the potential difference formed between the dissimilar metals of the first longitudinal strip 960, the second longitudinal strip 962, the third longitudinal strip 964, and the fourth longitudinal strip 966.

Although the above embodiments illustrate the inner member 954 being formed from four longitudinal strips of dissimilar metals, it will be understood by one of ordinary skill in the art that a greater number or a fewer number of longitudinal strips may be used to form a composite wire. A minimum of two longitudinal ribbons or strips of dissimilar metals are required such that galvanic coupling takes place therebetween when exposed to bodily fluids and the galvanic coupling induces a voltage or potential difference which inhibits or controls cell proliferation as described above.

Figure 11:
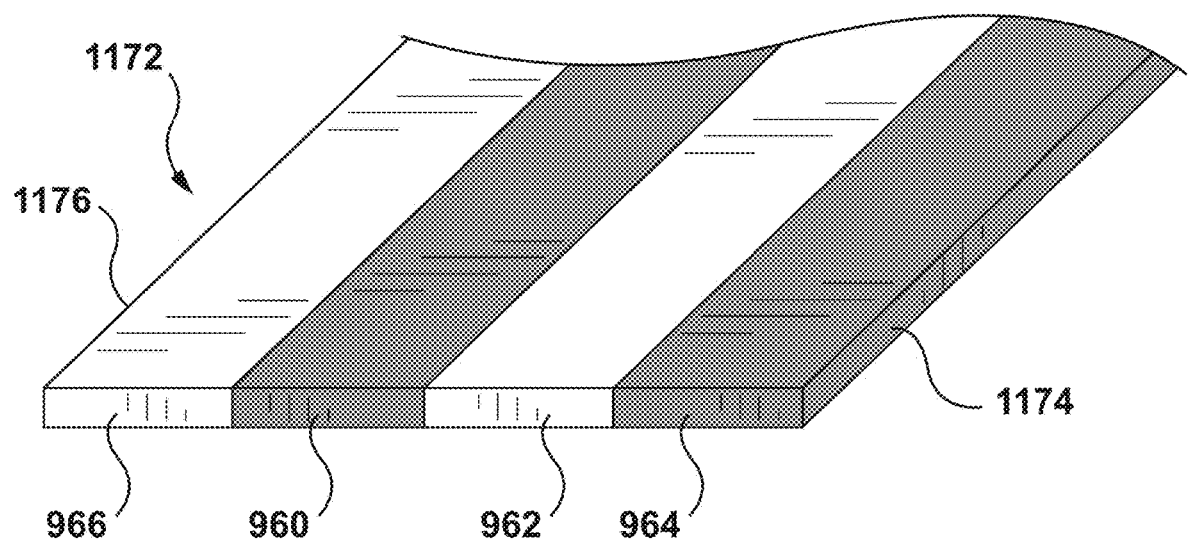
FIG. 11 is a schematic illustration of a planar structure that forms the inner member of FIG. 9 after manufacturing thereof.
Figure 12:
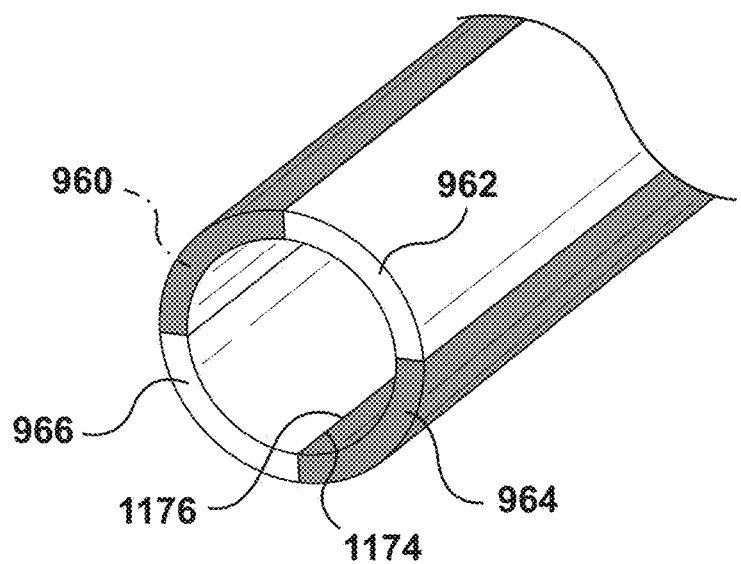
FIG. 12 is a schematic illustration of the planar structure of FIG. 11 formed into a tubular element.

FIG. 11 is a schematic illustration of a portion of a flat or planar structure 1172 that forms the inner member 954 after manufacturing thereof, while FIG. 12 is a schematic illustration of the planar structure 1172 formed into a tubular element. To form the planar structure 1172, the first longitudinal strip 960, the second longitudinal strip 962, the third longitudinal strip 964, and the fourth longitudinal strip 966 are joined together or attached to each other, such as by welding, soldering, fusion, adhesive, or other various methods, thereby forming planar structure 1172 as shown in FIG. 11. The planar structure 1172 may then be rolled such that a first longitudinal edge 1174 and a second longitudinal edge 1176 are rolled towards each other, as shown in FIG. 12. First longitudinal edge 1174 and second longitudinal edge 1176 may then be joined together or attached to each other, such as by welding, soldering, fusion, adhesive, or other various methods, thereby forming a tubular element that is the inner member 954 when assembled into composite wire 950.

A method for forming stent 900 in accordance with an embodiment hereof includes utilizing a hollow composite wire 950 having the inner member 954 and the outer member 952, as described above and shown schematically in FIG. 9A. Hollow composite wire 950 may be formed by any suitable method of forming composite wires. For example, and not by way of limitation, hollow composite wire 950 may be formed by a co-drawing process, extrusion, cladding, or any other suitable method. Hollow composite wire 950 is then shaped into a stent pattern. As discussed above, the stent pattern can be the pattern shown in FIG. 9 or any other suitable pattern formed from a wire. In an embodiment, shaping the hollow composite wire 950 into the stent pattern shown in FIG. 9 generally includes the steps of forming hollow composite wire 950 into a two dimensional generally sinusoidal waveform pattern followed by wrapping the pattern around a mandrel. The end result is a helical stent pattern formed onto a mandrel. Selected crowns 914 of the helical pattern may then be fused together and the stent may be removed from the mandrel. The step of shaping hollow composite wire 950 into the stent pattern can be performed using various techniques. For example, and not by way of limitation, forming the hollow composite wire 950 into a two-dimensional waveform can be achieved using techniques described in U.S. Application Publication Nos. 2010/0269950 to Hoff et al., 2011/0070358 to Mauch et al., and 2013/0025339 to Costa et al., each of which is incorporated in its entirety by reference herein.

Figure 10:
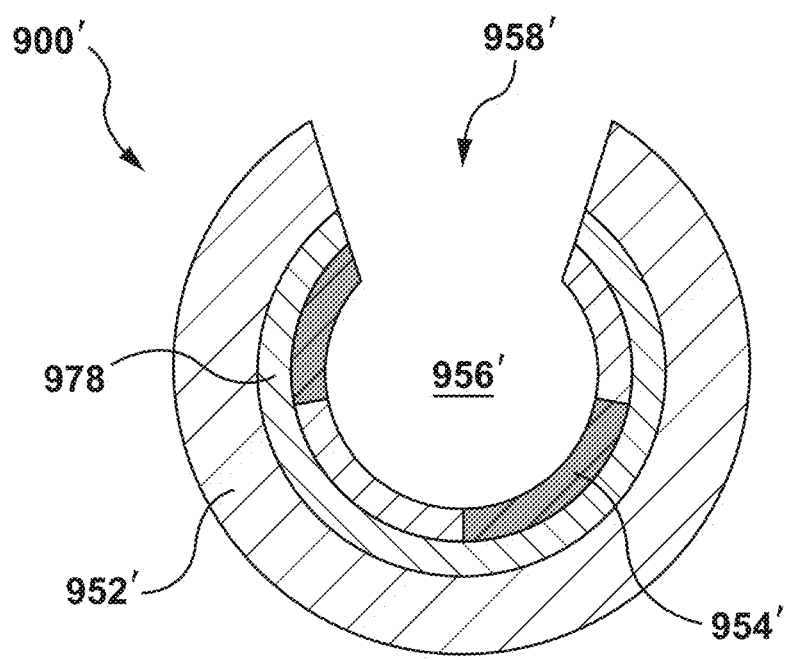
FIG. 10 is schematic cross-sectional view taken along line A-A of FIG. 9 according to another embodiment hereof.

Although the stent 900 has been described herein as formed from a bi-layer composite wire with an outer member and an inner member, this is not meant to be limiting, and it will be understood that in an alternate embodiment, a stent 900' may be formed from a tri-layer composite wire. As shown in FIG. 10, which is a cross-sectional view of the stent 900' formed of a tri-layer composite wire, the tri-layer composite wire embodiment of the stent 900' generally includes an outer member 952', an intermediate member 978 lining at least a portion of the outer member 952', and an inner member 954'. Openings 958' are disposed through the outer member 952', the intermediate member 978, and the inner member 954' to the lumen 956'. The intermediate member 978 may be formed of a radiopaque material to permit the stent 900' to be visible under X-ray or fluoroscopic imaging equipment when the outer member is made of a material that is difficult to visualize under X-ray or fluoroscopic imaging equipment.

Figure 13:
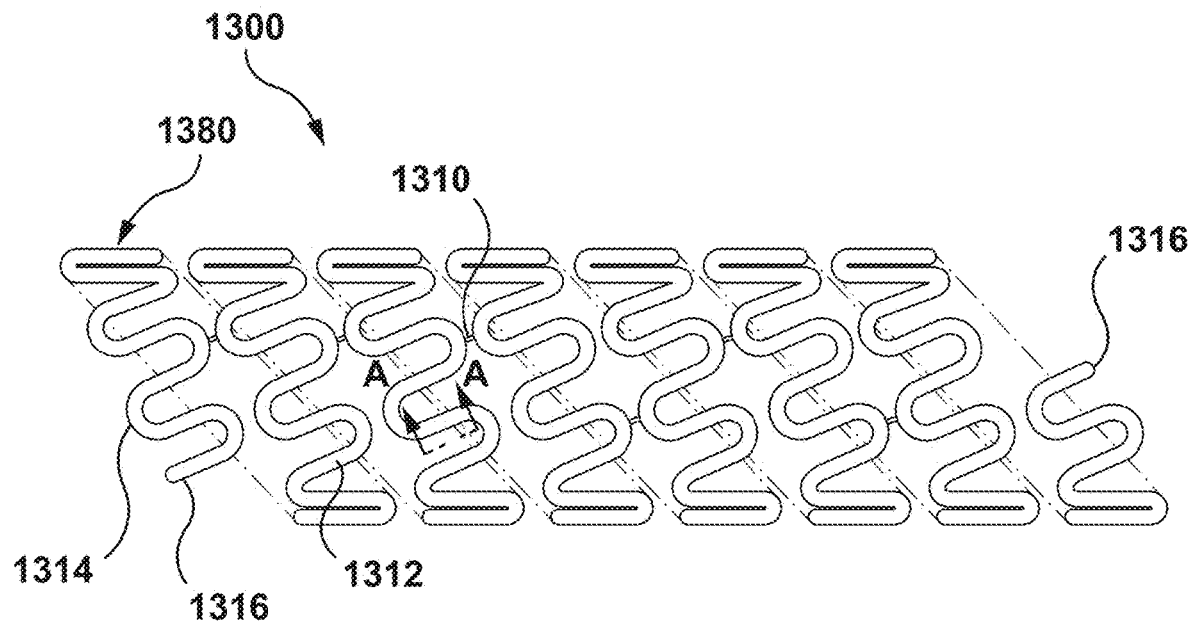
FIG. 13 is a schematic illustration of stent according to another embodiment hereof, wherein the stent is formed from a composite wire that includes a first wire stacked on top of a second wire and a plurality of windows along a length of the composite wire, wherein an insert is disposed within each window of the plurality of windows.
Figure 14:
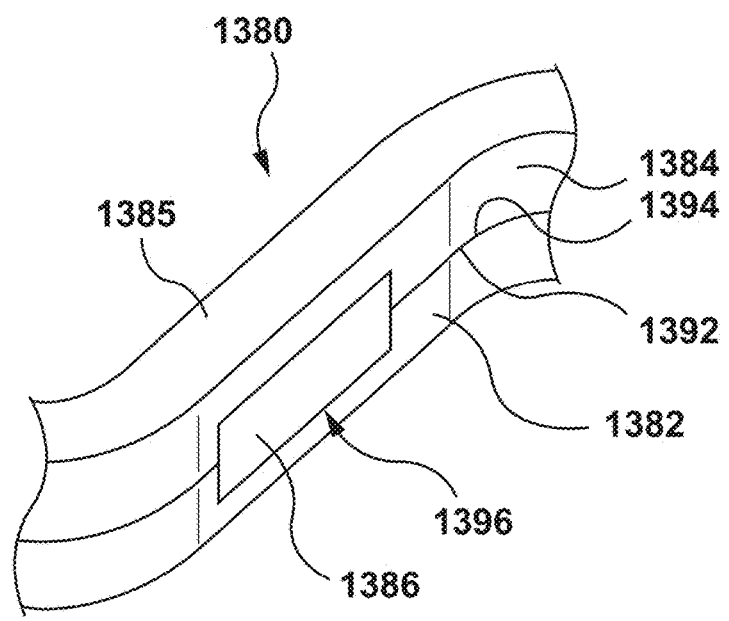
FIG. 14 is an enlarged view of a portion of the composite wire of FIG. 13.

FIG. 13 is a schematic illustration of a stent 1300 according to another embodiment hereof. FIG. 14 is schematic sectional view taken along line A-A of FIG. 13. The stent 1300 is formed from a composite wire 1380 that includes a first wire 1382 stacked directly on top of a second wire 1384 and a plurality of inserts 1386 embedded between the first and second wires 1382, 1384 as will be described in more detail herein. Composite wire 1302 is helically wound into the stent 1300 such that the stent 1300 has a tubular configuration as shown on FIG. 13. More particularly, the composite wire 1302 is formed into a series of generally sinusoidal waveforms including generally straight segments or struts 1312 joined by bent segments or crowns 1314 and the waveform is helically wound to form a generally tubular stent 1300. In the embodiment shown in FIG. 13, selected crowns 1314 of longitudinally adjacent sinusoids may be joined by, for example, fusion points 1310. Further, ends 1316 of composite wire 1302 may be welded, crimped or otherwise connected to other portions of composite wire 1302 such that the ends 1316 are not free ends. Ends 1316 may alternatively be provided as free ends, as shown in FIG. 13. The invention hereof is not limited to the pattern shown in FIG. 13. The composite wire 1302 of the stent 1300 can be formed into any pattern suitable for use as a stent. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

Figure 15:
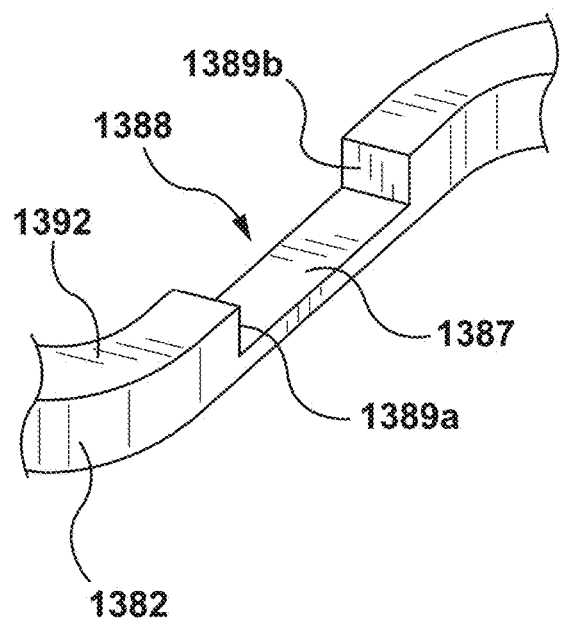
FIG. 15 is a schematic illustration of the first wire of FIG. 14, wherein the first wire is shown removed from the composite wire for illustrative purposes only.
Figure 16:
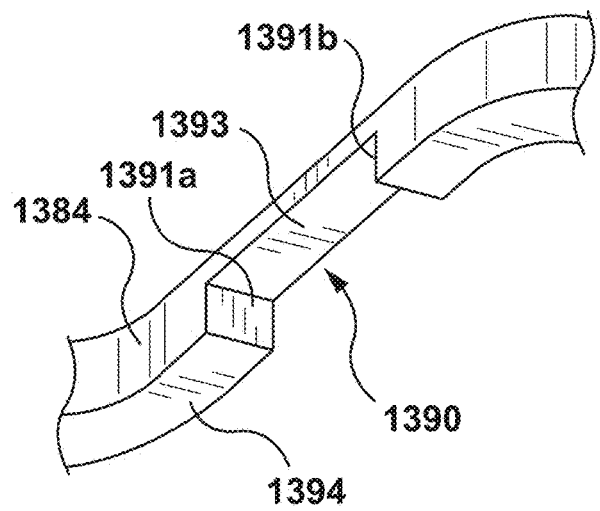
FIG. 16 is a schematic illustration of the second wire of FIG. 14, wherein the second wire is shown removed from the composite wire for illustrative purposes only.
Figure 17:
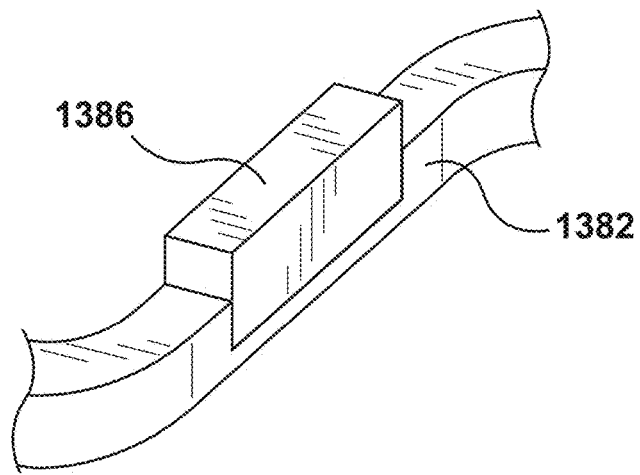
FIG. 17 is a schematic illustration of the second wire and the insert of FIG. 14, wherein the second wire and the insert are shown removed from the composite wire for illustrative purposes only.

Each of the first wire 1382 and the second wire 1384 has a rectangular cross-section. In addition, as best shown in FIGS. 15-16, each of the first wire 1382 and the second wire 1384 has a plurality of indentations, notches, or recesses 1388, 1390, respectively, formed on abutting surfaces 1392, 1394, respectively, thereof. As shown on FIG. 15, recesses 1388 of the first wire 1382 are defined by a first sidewall surface 1389a and a second sidewall surface 1389b of the first wire 1382. A bottom surface 1387 of each recess 1388 extends between the first sidewall surface 1389a and the second sidewall surface 1389b. Bottom surface 1387 is recessed from abutting surface 1392 of the first wire 1382 where the first wire 1382 is not recessed. Similarly, as shown on FIG. 16, recesses 1390 of the second wire 1384 are defined by a first sidewall surface 1391a and a second sidewall surface 1391b of the second wire 1384. A bottom surface 1393 of each recess 1390 extends between the first sidewall surface 1391a and the second sidewall surface 1391b. Bottom surface 1393 is recessed from abutting surface 1394 of the second wire 1384 where the second wire 1384 is not recessed. Although recesses 1388, 1390 are shown with vertical sidewall surfaces and a rectangular cross-section, recesses 1388, 1390 may be of any desired shape and the sidewall surfaces may be, for example, angled. Recesses 1388, 1390 may be formed by various methods, such as, but not limited to, photolithography techniques or wet or dry etching.

As best shown in FIG. 14, when first and second wires 1382, 1384 are assembled to form composite wire 1380, the plurality of recesses 1388 of the first wire 1382 are longitudinally aligned with the plurality of recesses 1390 of the second wire 1384 to form a plurality of windows 1396 along a length of the composite wire 1380. In an embodiment, the plurality of windows 1396 are longitudinally spaced apart at equal intervals along the length of the composite wire 1380. In addition, with reference to FIG. 13 and FIG. 14, in an embodiment the plurality of windows 1396 are positioned on the generally straight segments or struts 1312 of the generally sinusoidal waveform of the composite wire 1380.

An insert 1386 is disposed within each window 1396. The insert 1386 is attached to each of the first wire 1382 and the second wire 1384. More particularly, the insert 1386 is preferably in contact with and attached to the first sidewall surface 1389a, the second sidewall surface 1389b, and the bottom surface 1387 of the recess 1388 of the first wire 1382 as well as in contact with and attached to the first sidewall surface 1391a, the second sidewall surface 1391b, and the bottom surface 1393 of the recess 1390 of the second wire 1384. However, it will be understood that the insert is only required to be attached to one surface of each of the recess 1388 of the first wire 1382 and the recess 1390 of the second wire 1384.

In addition to the first wire 1382 and the second wire 1384, the composite wire 1380 may further include a third wire 1385 as shown in FIG. 14. The third wire 1385 also has a rectangular cross-section and is stacked directly on top of the second wire 1384, i.e., stacked in a radial direction. The third wire 1385 may be any material that is suitable to be used as a stent. For example, and not by way of limitation, the third wire 1385 may be a cobalt-chromium alloy. The third wire 1385 may be included to add additional strength to the composite wire 1380 but is not required. For example, the third wire 1385 adds additional strength to the composite wire 1380 and also assists in holding the insert 1386 mechanically in place. The third wire 1385 may also be configured to modify the ratio between dissimilar metals and the associated or resulting potential. In another embodiment, the third wire 1385 may be omitted.

Stent 1300 is configured to control tissue growth of the tissue surrounding stent 1300 after implantation. More particularly, the first wire 1382, the second wire 1384 and the plurality of inserts 1386 are formed from dissimilar metals such that galvanic coupling takes place therebetween when exposed to bodily fluids. The materials of the first wire 1382, the second wire 1384 and the plurality of inserts 1386 are selected such that a galvanic coupling occurs between each wire and the insert and the galvanic coupling induces a voltage or potential difference which inhibits or controls cell proliferation. In an embodiment, the first wire 1382 and the second wire 1384 are each made from a relatively more noble material such as platinum, a platinum-iridium alloy, tantalum, tungsten, or gold. In an embodiment, the plurality of inserts 1386 are each made relatively less noble material such as a cobalt-chromium alloy, magnesium, or zinc.

In the embodiment described above, the plurality of inserts 1386 is less noble (more active) than each of the first wire 1382 and the second wire 1384 made from a more noble material. Each insert 1386 is sandwiched or embedded between the first wire 1382 and the second wire 1384, and thus each insert 1386 is in contact with the first wire 1382 and the second wire 1384. Thus, each insert 1386 acts as an anode and experiences galvanic coupling as a result of its contact with the first wire 1382 and the second wire 1384 made from a more noble material. A potential difference is formed between the more noble material of the first wire 1382 and the second wire 1384 and the less noble material of the plurality of inserts 1386, and the formed or induced potential differences inhibits cell proliferation and thereby controls or limits excessive tissue growth around the stent 1300 after implantation. More particularly, when the stent 1300 is deployed within a vessel, cells attach or couple to the outer surface of composite wire 1380. Once attached thereto, the cells grow or colonize and form an extracellular matrix on the outer surface of composite wire 1380 to couple the stent 1300 to the vessel. The mechanical integration, or coupling of the stent 1300 to the vessel may offer clinical benefit in reducing micro-damage to the tissue surrounding the stent 1300 during biomechanical motion of the vessel, such as the repetitive constriction and dilation of the vessel due to cardiac pressure differentials of the cardiac cycle. However, excessive tissue growth and restenosis is avoided due to the potential difference formed between the dissimilar metals of the first wire 1382, the second wire 1384 and the plurality of inserts 1386.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent configured to control tissue growth, the stent comprising:
    a composite wire helically wound into a tubular configuration, wherein the composite wire is formed from a first wire and a second wire nested within each other in a circumferential direction and coupled together only at distinct fusion points, the first wire being shaped into a first sinusoidal waveform including a plurality of straight segments and a plurality of bent segments and the second wire being shaped into a second sinusoidal waveform including a plurality of straight segments and a plurality of bent segments, the bent and straight segments of the second sinusoidal waveform to fit within the bent and straight segments of the first sinusoidal waveform such that the second waveform is nested in the circumferential direction within the first waveform, and
    wherein the first and second wires are formed from dissimilar metals such that a potential difference is formed when the dissimilar metals are exposed to bodily fluids, the potential difference being configured to inhibit cell proliferation and thereby control tissue growth around the stent after implantation.

2. The stent of claim 1, wherein at least some of the bends of the first sinusoidal waveform are fused to at least some of the bends of the second sinusoidal waveform forming the fusion points.

3. The stent of claim 2, wherein at least some of the straight segments of the first sinusoidal waveform are not fused to at least some of the straight segments of the second sinusoidal waveform.

4. The stent of claim 1, wherein the composite wire further includes a third wire coupled to the first wire, the third wire being formed from a dissimilar metal from the first wire such that a potential difference is formed between the first and third wires when the first and third wires are exposed to bodily fluids, and wherein the third wire is shaped into a third sinusoidal waveform including a plurality of straight segments and a plurality of bent segments, the bent and straight segments of the first sinusoidal waveform fit within the bent and straight segments of the third sinusoidal waveform such that the first sinusoidal waveform is nested in the circumferential direction within the third sinusoidal waveform.

5. The stent of claim 4, wherein the first wire is formed from a material selected from tantalum, tungsten, platinum, a platinum-iridium alloy, and gold and each of the second wire and the third wire is formed from a material selected from a cobalt-chromium alloy, magnesium, a magnesium alloy, and zinc.

6. The stent of claim 5, wherein the second wire and the third wire are formed from the same material.

7. The stent of claim 5, wherein the second wire and the third wire are formed from different materials.

8. The stent of claim 5, wherein each of the first, second, and third wires has a circular cross-section.

9. The stent of claim 5, wherein each of the first, second, and third wires is the same size.

10. The stent of claim 1, wherein the first wire is formed from a material selected from tantalum, tungsten, platinum, a platinum-iridium alloy, and gold and the second wire is formed from a material selected from a cobalt-chromium alloy, magnesium, a magnesium alloy, and zinc.

11. The stent of claim 1, wherein each of the first and second wires has a circular cross-section.

12. The stent of claim 1, wherein each of the first and second wires is the same size.

13. A stent configured to control tissue growth, the stent comprising:
    a composite wire helically wound into a tubular configuration, the composite wire being formed from a first wire, a second wire, and a third wire nested within each other, wherein
    the first wire is shaped into a first sinusoidal waveform including a plurality of straight segments and a plurality of bent segments,
    the second wire is shaped into a second sinusoidal waveform including a plurality of straight segments and a plurality of bent segments, the bent and straight segments of the second sinusoidal waveform to fit within the bent and straight segments of the first sinusoidal waveform such that the second waveform is configured to nested within the first waveform, and
    the third wire is shaped into a third sinusoidal waveform including a plurality of straight segments and a plurality of bent segments, the bent and straight segments of the first sinusoidal waveform fit within the bent and straight segments of the third sinusoidal waveform such that the first sinusoidal waveform is nested within the third sinusoidal waveform to nest within the first waveform, and the first wire, the second wire, and the third wire are directly beside each other and only coupled to each other at distinct points in a circumferential direction with the first wire disposed between the second and third wires, and
    wherein each of the second and third wire is formed from a dissimilar metal than the first wire such that a potential difference is formed when the dissimilar metals are exposed to bodily fluids, the potential difference being configured to inhibit cell proliferation and thereby control tissue growth around the stent after implantation.

14. The stent of claim 13, wherein at least some of the bends of the first sinusoidal waveform are fused to at least some of the bends of each of the second and third sinusoidal waveforms.

15. The stent of claim 14, wherein at least some of the straight segments of the first sinusoidal waveform are not fused to at least some of the straight segments of each of the second and third sinusoidal waveforms.

16. The stent of claim 13, wherein the first wire is formed from a material selected from tantalum, tungsten, platinum, a platinum-iridium alloy, and gold and each of the second wire and the third wire is formed from a material selected from a cobalt-chromium alloy, magnesium, a magnesium alloy, and zinc.

17. The stent of claim 16, wherein the second wire and the third wire are formed from the same material.

18. The stent of claim 16, wherein the second wire and the third wire are formed from different materials.

19. The stent of claim 13, wherein each of the first, second, and third wires has a circular cross-section.

20. The stent of claim 13, wherein each of the first, second, and third wires is the same size.

* * * * *